United States Patent
Ray, Sr.

[11] Patent Number: 5,597,305
[45] Date of Patent: Jan. 28, 1997

[54] DENTAL WRENCH

[76] Inventor: Charles M. Ray, Sr., 12755 Nemo Rd., Rapid City, S. Dak. 57702

[21] Appl. No.: 489,230
[22] Filed: Jun. 12, 1995
[51] Int. Cl.[6] ................................................. A61C 3/00
[52] U.S. Cl. ............................................. 433/141; 81/467
[58] Field of Search .......................... 433/141; 81/479, 81/477, 471, 478, 480, 481, 467, 468

[56] References Cited

U.S. PATENT DOCUMENTS

| | | | |
|---|---|---|---|
| 2,289,238 | 7/1942 | Brunelle | 81/477 |
| 2,553,311 | 5/1951 | Greer | 81/477 |
| 3,283,620 | 11/1966 | Bailey | 81/52.4 |
| 3,967,513 | 7/1976 | Myrdal | 81/477 |
| 4,314,490 | 2/1982 | Stone | 81/479 |
| 4,480,997 | 11/1984 | Deutsch et al. | 433/221 |
| 4,664,001 | 5/1987 | Denman | 81/479 |
| 4,838,134 | 6/1989 | Ruland | 81/467 |
| 5,158,458 | 10/1992 | Perry | 433/141 |
| 5,295,831 | 3/1994 | Patterson et al. | 433/141 |

FOREIGN PATENT DOCUMENTS 2255878  9/1973  Germany ................................ 81/477

*Primary Examiner*—Cary E. O'Connor
*Attorney, Agent, or Firm*—Gene R. Woodle

[57] ABSTRACT

Embodiments of a dental wrench are disclosed which may be used to tighten or loosen screws used for dental components and which may further be used to determine the amount of torque applied to such a screw and the amount of torque necessary to loosen such a screw.

1 Claim, 2 Drawing Sheets

DENTAL WRENCH

BACKGROUND OF THE INVENTION

1. Field of the Invention

The present invention relates generally to restorative dentistry and more particularly to torque wrenches for dental components.

1. Background Information

The use of dental restorations to replace missing teeth and techniques for such use are well known in the prior art. One of these techniques requires that one or more implants be affixed to either the maxillary or the mandibular bone of a patient. Such implants are typically cylindrical and are internally screw threaded. A casting is made which fits over one or more implants. The casting is held in place by a screw which passes through the casting and screws into the threaded portion of the implant. In many cases two such screws are necessary, because the casting is attached to two implants. Castings typically include some type of fastening system for attachment of dental prostheses. Such a screw typically includes an internal hex opening or slot in the end opposite the threads. A driver with either a hex head or blade matching the opening or slot in the screw is typically used to tighten the screw.

A problem is always encountered in the technique of using implants and castings as described above: applying the correct torque on the driver to provide the appropriate screw tightness. If the screw or screws holding the casting are too loose, the dental prosthesis will be loose or may become displaced. If too much torque is applied to a screw, the screw may be fractured or weakened to the point that it will fail in the future. In those cases in which one casting is attached to two or more implants, it is also very important that the same torque be applied to each of the attaching screws to prevent undue pressure on any of the implants. A similar problem encountered when one casting is attached to two or more implants is that the fit of the casting must be passive. That is, even though the screws attaching the casting may be tightened to the same torque, the screws, implants, and the casting will be subjected to unacceptable stress if the casting is bent or twisted after it is installed. A passive fit may be assured by adjusting the casting so that each of the screws is tightened to the appropriate torque after being turned approximately the same number of revolutions or part of a revolution from being finger tight.

Several attempts have been made to solve the aforementioned problems. One such attempt is disclosed in the patent to Deutsch et al. (U.S. Pat. No. 4,480,997, Nov. 6, 1984). The Deutsch patent discloses a wrench used to apply a predetermined torque to a dental post. The wrench has a cylindrical casing designed to be turned with the thumb and index finger. A clutch inside the casing may be adjusted so that the wrench slips when a predetermined torque is reached.

Another attempt to solve problems related to dental screw torque is disclosed in the patent to Perry (U.S. Pat. No. 5,158,458, Oct. 27, 1992). The device disclosed in Perry includes a driver portion which engages the screw and a mandrel to which the turning force is applied. A torque element is interposed between the driver and the mandrel which engages with each of them. The torque element includes an inner member which engages the mandrel and an outer member which engages the driver. The inner and outer members are connected by spokes. When the torque between the driver and the mandrel reaches a predetermined level the spokes break indicating that a particular torque has been applied to the screw.

Another attempt to solve problems related to dental screw torque is disclosed in the patent to Patterson et al. (U.S. Pat. No. 5,295,831, Mar. 22, 1994). The device disclosed in Patterson is essentially an Allen wrench with a calculated weak spot built into one of the legs. When a screw is being tightened using the wrench and a predetermined torque is reached, the weakened spot gives way and the wrench deforms.

Another problem associated with the use of torque wrenches for tightening a dental component is the necessity for sterilization. Only sterile dental implements and devices should be introduced into a patient's mouth Another problem associated with the use of torque wrenches for dental components is the occasional necessity to determine the torque required to loosen a screw which attaches a dental component. This may be necessary, for example, when a single casting is affixed to two implants by means of two screws and the screws should be tightened to the same torque.

All of the known dental wrenches require either that a different wrench or element be chosen or that an adjustment be made to the wrench to measure differing toques. Several of the know dental wrenches may only be used once or require replacement of an element with each use. Other dental wrenches require a variety of relatively complicated moving or interacting parts or are difficult to clean or sterilize. The ideal wrench for applying a measured torque to a dental component is compact, lightweight, easy to use, usable for many different torque requirements, and has few, if any, moving or interacting parts. Another requirement of the ideal dental torque wrench is that it be easily cleaned and sterilized. Another requirement of the ideal dental torque wrench is that it may be used to determine the torque necessary to loosen the screw on a dental component as well as the torque necessary to tighten such a screw.

SUMMARY OF THE INVENTION

The dental wrench of the instant invention solves the problems associated with the application of measured torque to a dental component One major objective of the dental wrench is to provide a torque wrench which may be used to apply measured torque to a dental component.

Another objective of the dental wrench is to provide a torque wrench which may be used to apply differing torques to a dental component without the necessity of using a different wrench, wrench element, or making an adjustment to the wrench.

Another objective of the dental wrench is to provide a torque wrench which may be used to measure the amount of torque necessary to loosen a dental component.

Another objective of the dental wrench is to provide a torque wrench which may be used to apply measured torque to a dental component which is easy to clean and sterilize.

Another objective of the dental wrench is to provide a torque wrench which may be used to apply measured torque to a dental component which is reusable, compact, lightweight, easy to use, and which has few moveable or interacting parts.

Another objective of the dental wrench is to provide a torque wrench which may be used to insure that a casting attached to two or more implants is attached with a passive fit.

DESCRIPTION OF A PREFERRED EMBODIMENT

Figure 1:
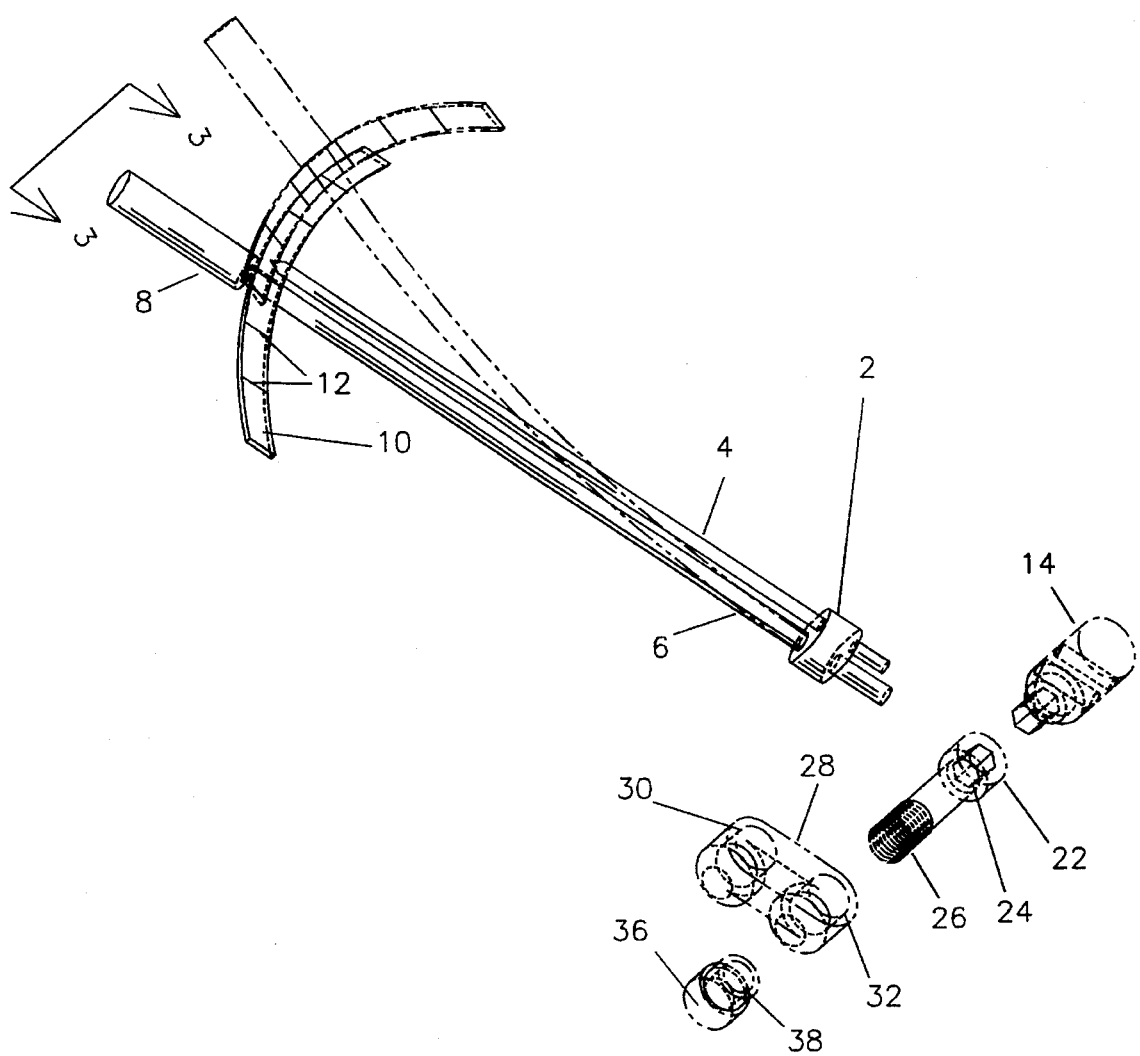
FIG. 1 is a perspective view of a preferred form of a dental wrench embodying the present invention.
Figure 2:
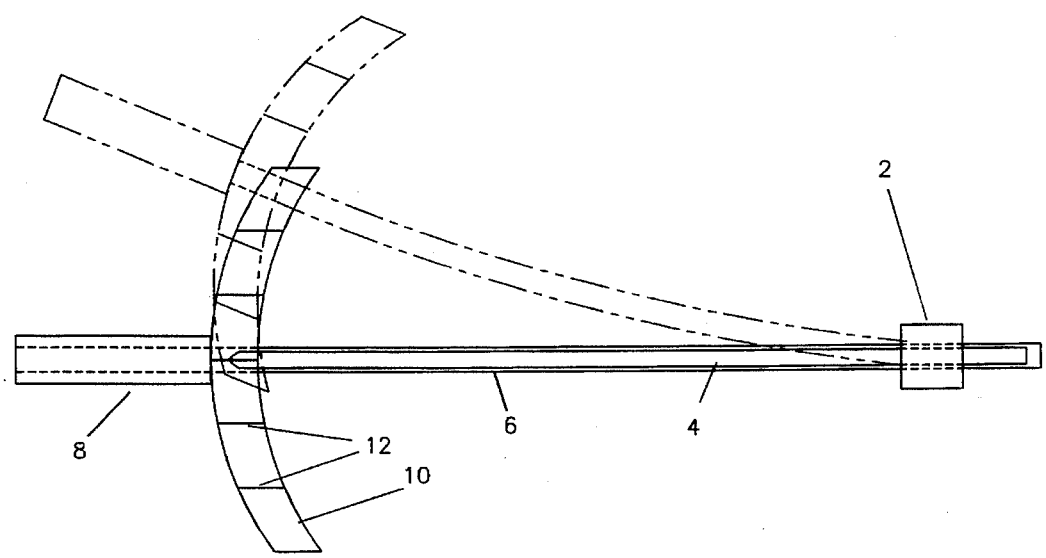
FIG. 2 is a top-plan view of the dental wrench of FIG. 1.
Figure 3:
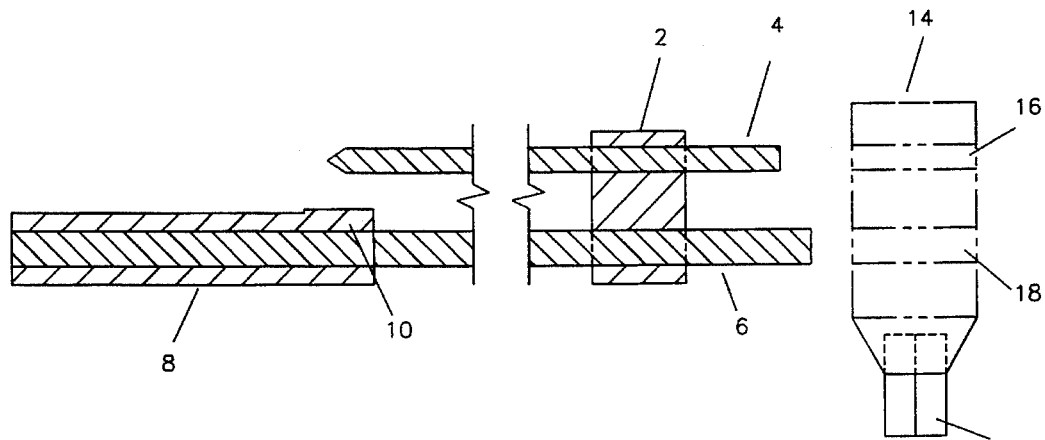
FIG. 3 is a sectional view of the dental wrench taken along line 3—3 of FIG. 1.

Referring to the drawings, FIGS. 1, 2, and 3, there is shown a preferred form of the dental wrench embodying the present invention.

Referring to FIG. 3, there is a joint block 2 having the general shape of a cube and having a forward face, a rearward face, a top, and a bottom. An indicator rod 4 having a cylindrical shape passes through a hole near the top of the joint block 2, the hole opening in the forward face and the rearward face of said joint block 2. The indicator rod 4 is of sufficient length that a small portion of the length of said indicator rod extends beyond the forward face of said joint block 2 and a greater portion of the length of said indicator rod 4 protrudes beyond the rearward face of said joint block 2. The rearward end of said indicator rod 4 comes to a point.

A torque rod 6 having a cylindrical shape passes through a hole near the bottom of said joint block 2, the hole opening in the forward face and the rearward face of said joint block 2 such that the torque rod 6 is beneath and parallel with said indicator rod 4. Said torque rod 6 protrudes from the forward face of said joint block 2 a slightly longer distance than said indicator rod 4. A handle 8 having a generally cylindrical shape has an interior hole slightly larger in diameter than the diameter of said torque rod 6 along the longitudinal axis of the handle 8. Said torque rod 6 is approximately the same length as the length of said indicator rod 4 added to the length of said handle 8 and fits inside the hole in said handle 8 such that the rearward end of said torque rod 6 is flush with the rearward end of said handle 8.

Referring now to FIG. 2, a scale 10 is affixed to the top of said torque rod 6 just forward of said handle 8. The scale 10 has the general shape of an arc with the center of the arc being the point at which the top of said torque handle 6 contacts the rearward face of said joint block 2. Said scale 10 is located between the top of said torque rod 6 and the bottom of said indicator rod 4. The distance between said torque rod 6 and said indicator rod 4 is such that the bottom of said indicator rod 4 is slightly above the top surface of said scale 10. A plurality of torque indicator marks 12 are on the top surface of said scale 10. The torque indicator marks 12 are roughly parallel to the longitudinal axis of said indicator rod 4. The rearward end of said indicator rod 4 protrudes slightly beyond the forrward edge of said scale 10.

Referring now to FIG. 1, a driver 14, screw 22, casting 28, and implant 36, are typical of those used in many conventional methods of dental restoration. The implant 36 is affixed directly to the jawbone of the patient. The casting 28 fits over said implant 36 and is held in place by the screw 22. Only one said implant 36 is shown, but in the case of a double casting as is depicted by said casting 28 two implants such as said implant 36 would be used, one in hole 30 in said casting 28 and one in hole 32 is said casting 28. In such cases two screws such as said screw 22 would be used. Said screw 22 is threaded at one end as shown by threads 26 The threads 26 are engaged with internal threads 38 in said implant 36. The end of said screw 22 opposite said threads 26 includes a means for engaging with the driver 14. A hex opening 24 is shown, but a slot or other engaging method may be used. Said driver 14 is engaged with hex opening 24 and is used to tighten said screw 22 within said implant 36. The engaging portion of said driver 14 is shown as a hex head, but it could be a blade or other appropriate shape to conform with the engaging portion of said screw 22.

Referring again to FIG. 3, a conventional driver 14 is shown. A hole 16 and a hole 18 may have to be drilled through said driver 14. The holes 16 and 18 are perpendicular to the longitudinal axis of said driver 14, are parallel, and are the same distance apart as said indicator rod 4 and said torque rod 6. The diameter of said hole 16 is slightly greater than the diameter of said indicator rod 4 and the diameter of said hole 18 is slightly greater than the diameter of said torque rod 6. In some instances the length of a conventional driver such as is depicted as said driver 14 is such that a slot is made in the top of said driver 14 and such slot performs the same function as said hole 16. When the dental wrench is in use the forward end of said indicator rod 4 is inserted into said hole 16 and the forward end of said torque rod 6 is inserted into said hole 18. A hex head 20 is inserted into the hex opening 24 of said screw 22. In cases in which the engaging portion of said screw 22 is configured as a slot or other opening, a matching configuration is used instead of the hex head 20.

Referring again to FIG. 1, in operation the thumb and index finger of the operator grasp said handle 8 and apply force in a clockwise direction which causes said driver 14 to rotate in a clockwise direction. Said driver 14 is engaged with said screw 22 and said screw 22 tightens within said implant 36 and holds said casting 28 in place. When said screw 22 becomes tight, the force on said handle 8 causes said torque rod 6 to begin to bend as is shown by the phantom lines indicating the movement of said torque rod 6, said handle 8, and said scale 10. Because no force is exerted upon the rearward end of said indicator rod 4, said indicator rod 4 does not bend. Said torque indicator marks 12 on the top of said scale 10 are calibrated such that the torque on said screw 22 may be measured by reading the position of said indicator rod 4 against said scale indicator marks 12 when said torque rod 6 is bent. The greater the deflection of said torque rod 6, the greater the torque. When said screw 22 is tightened to the appropriate torque, said driver 14 and the dental wrench are removed.

Screws such as said screw 22 may also be loosened by using the dental wrench as described above, but by applying force to said handle 8 in a counterclockwise direction. Said scale 10, scale indicator marks 12, and said indicator rod 4 may then be used to determine the amount of torque necessary to loosen said screw 22.

In the preferred embodiment of the dental wrench said torque rod 6 is made from titanium weld wire, said indicator rod 4 is made from stainless steel, and all other parts are made from type 4 crown and bridge dental alloy; but another metal could be used provided it is of sufficient strength, is lightweight, is corrosion resistant, and is capable of being heated to 600 degrees Fahrenheit for sterilization without negative effects. In the preferred embodiment of the dental wrench all joints and connections are soldered with silver solder, but other fastening methods could be used provided they were of sufficient strength, were corrosion resistant, and were capable of being heated to 600 degrees Fahrenheit without negative effects. All parts, joints, and connections must be made such that they are safe for use for dental applications. In the preferred embodiment said scale 10 and said handle 8 are cast in one piece, but they could be made separately and soldered together. In the preferred embodiment said torque rod 6 fits inside the hole in said handle 8, but said torque rod 6 could be affixed in several other ways including being shorter by the length of said handle 8 and being soldered with the rearward end of said torque rod 6 abutting the forward end of said handle 8. The entire apparatus is plated with 24 karat gold after manufacture. Such plating ensures that the apparatus is safe for use in dental applications and that the apparatus may be sterilized. In the preferred embodiment, said indicator rod 4 and said torque rod 6 are cylindrical in shape; but other shapes could be used provided said holes 16 and 18 have the same shape.

While preferred embodiments of this invention have been shown and described above, it will be apparent to those skilled in the art that various modifications may be made in these embodiments without departing from the spirit of the present invention. For that reason, the scope of the invention is set forth in the following claims:

I claim:

1. A dental wrench for applying a measured torque to dental components comprising:

(1) a joint block having the general shape of a cube, the joint block having a forward face, a rearward face, a top, and a bottom; said joint block having two aligned, parallel holes passing from the forward face to the rearward face; one of said holes being near the top of said joint block; and one of said holes being near the bottom of said joint block;

(2) an indicator rod having a generally cylindrical shape, the indicator rod passing through the top hole in said joint block and having sufficient length that a small portion of the length of said indicator rod protrudes beyond the forward face of said joint block and a larger portion of the length of said indicator rod protrudes beyond the rearward face of said joint block;

(3) a torque rod having a generally cylindrical shape and having approximately the same length as said indicator rod, the torque rod passing through the bottom hole in said joint block and having a slightly longer length of said torque rod than the length of said indicator rod which protrudes beyond the forward face of said joint block protruding beyond the forward face of said joint block and a larger portion of the length of said torque rod protrudes beyond the rearward face of said joint block;

(4) a handle having a generally cylindrical shape and a diameter slightly greater than the diameter of said torque rod affixed to the rearward end of said torque rod with the longitudinal axis of the handle being aligned with the longitudinal axis of said torque rod;

(5) a scale having the general shape of an arc with the center of the arc being the point where the top of said torque rod contacts the rearward face of said joint block, the scale being affixed to the top of said torque rod just forward of said handle such that the bottom of said indicator rod is slightly above the top surface of said scale and the rearward end of said indicator rod protrudes slightly beyond the forward surface of said scale; and (6) scale indicator marks on the top surface of said scale, the scale indicator marks being roughly parallel to the longitudinal axis of said torque rod and said scale indicator marks being symmetrical about the longitudinal axis of said torque rod;

whereby when the forward ends of said indicator rod and of said torque rod are inserted into a driver and the driver is engaged with a screw used to fasten a dental component the dental wrench may be used by an operator grasping said handle and by applying force to said handle to apply torque to the screw and said torque rod bends from the force exerted upon said handle and the torque applied to the screw may be read by determining the position of said indicator rod relative to said scale indicator marks.

\* \* \* \* \*